(12) United States Patent
Chang et al.

(10) Patent No.: US 6,235,005 B1
(45) Date of Patent: May 22, 2001

(54) POSITIVE ENGAGEMENT-DISENGAGEMENT CATHETER SLEEVE

(75) Inventors: Joseph J. Chang, Irving, TX (US); Cathy J. Myers; Mark A. Panzera, both of Bristol, CT (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/222,573

(22) Filed: Dec. 28, 1998

(51) Int. Cl.[7] .................................................. A61M 5/00
(52) U.S. Cl. ...................................... 604/263; 604/165.02
(58) Field of Search ....................... 604/165.01–165.04, 604/263, 198

(56) References Cited

U.S. PATENT DOCUMENTS

| | | |
|---|---|---|
| 4,500,312 | 2/1985 | McFarlane . |
| 4,573,981 * | 3/1986 | McFarlane . |
| 4,790,827 * | 12/1988 | Haber et al. . |
| 5,106,379 * | 4/1992 | Leap . |
| 5,154,698 * | 10/1992 | Compagnucci et al. . |
| 5,219,339 | 6/1993 | Saito ..................................... 604/198 |
| 5,360,404 | 11/1994 | Novacek et al. ..................... 604/110 |

FOREIGN PATENT DOCUMENTS

| | | |
|---|---|---|
| 2 733 916 A1 | 11/1996 | (FR) . |
| WO 97/25082 | 7/1997 | (WO) . |

\* cited by examiner

*Primary Examiner*—Mark Bockelman
(74) *Attorney, Agent, or Firm*—Blakely, Sokoloff, Taylor & Zafman

(57) ABSTRACT

A positive engagement/disengagement catheter sleeve to reduce risks of needle sticks. The sleeve has a base and a body which define a pair of grooves. The grooves define a deformable region of the sleeve therebetween. At least one detent is provided inside the base within the deformable region. A mechanism is provided to cause the detent to disengage when the mechanism is actuated.

10 Claims, 3 Drawing Sheets

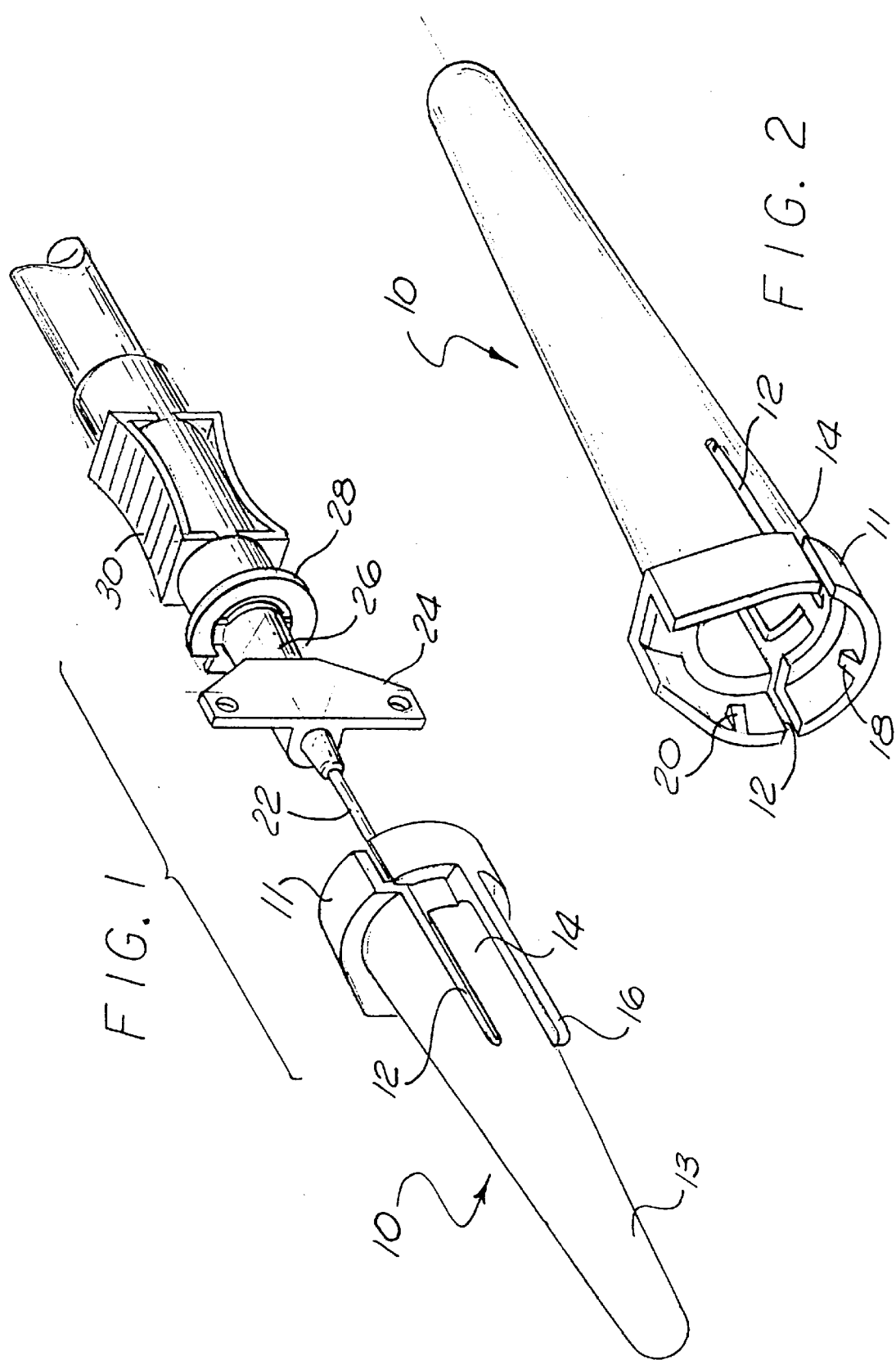

POSITIVE ENGAGEMENT-DISENGAGEMENT CATHETER SLEEVE

BACKGROUND (1) Field of the Invention

The invention relates to catheters. More specifically, the invention relates to a sleeve that positively engages an introducer to reduce the risk of unintentional needle sticks.

(2) Background

Catheters and sleeves therefor have been ubiquitous in the medical supplies market for some time. A typical catheter assembly arrives in sterile packaging and comprises a catheter, the introducer, and a sleeve. The purpose of the sleeve is to protect the needle tip during shipping and to prevent unintentional needle sticks as the catheter and introducer are removed from the sterile packaging. To that end, the sleeve needs to have sufficient retention force that it does not unintentionally become disengaged from the introducer as the sterile packaging is removed. However, if the retention force is too great, the incidence of needle pricks in the course of removing the sleeve actually increases. By way of example, a user typically grabs the sleeve in one hand and the introducer in the other, then pulling the sleeve in one direction and the introducer in the opposite direction, when the introducer snaps free, the arms of the user recoil, causing the user to inadvertently stick themself. This has been an area of substantial concern.

One common way of retaining the sleeve on the introducer is to mold three detents into the sleeve to engage an annular flange on the introducer. This works adequately for certain types of catheters. However, catheters have been developed that have wings that permit the catheter to be more easily secured to a patient after introduction. These wings necessitate grooves in the sleeve to accommodate the wings while the catheter is sleeved. With the introduction of the grooves, the structural integrity of the sleeve is such that disengagement from the detents is highly likely, as only a very loose hold is possible. Attempts to accommodate this problem by increasing the size of the detent between the grooves has resulted in cases of both an unreliable hold and too strong a hold, both resulting in increased risk for unintentional needle sticks.

BRIEF SUMMARY OF THE INVENTION

A positive engagement/disengagement catheter sleeve to reduce risks of needle sticks is disclosed. The sleeve has a base and a body which define a pair of grooves. The grooves define a deformable region of the sleeve therebetween. At least one detent is provided inside the base within the deformable region. A mechanism is provided to cause the detent to disengage when the mechanism is actuated.

BRIEF DESCRIPTION OF THE DRAWINGS

FIG. 1 is a perspective view of a catheter with introducer and sleeve of one embodiment of the invention.

FIG. 2 is a perspective view of the sleeve of the embodiment of FIG. 1.

DETAILED DESCRIPTION

Figure 3:
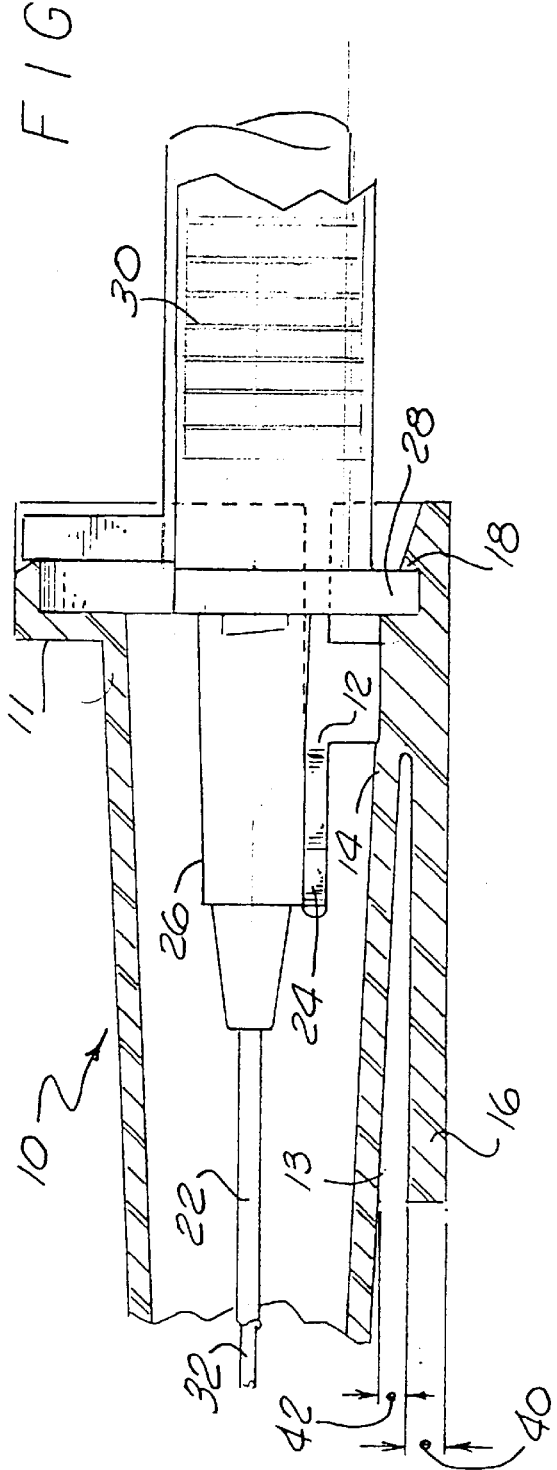
FIG. 3 is a partial cross-section view of the catheter assembly and sleeve of the embodiment of FIG. 1.

FIG. 1 is a perspective view of a catheter with introducer and sleeve of one embodiment of the invention. The catheter 22 is coupled to a catheter hub 26. Hub 26 has wings 24 formed as part thereof. Introducer 30 has an annular flange 28 as part thereof to engage sleeve 10. Sleeve 10 has a pair of grooves 12 disposed to receive the wings 24 of catheter hub 26. Sleeve 10 has a base 11 at an insertion end and a body 13 terminating in a distal end. The grooves define a deformable region 14 therebetween. Attached to the deformable region 14 is an arm 16. Arm 16 has a first end where it attaches to the deformable region 16 and a free end down the sleeve from the base. Pressure on the arm 16 at its distal end causes the deformable region at the base to move away from an axis of the sleeve.

FIG. 2 is a perspective view of the sleeve of the embodiment of FIG. 1. A plurality of detents 18, 20 are disposed within base 11. While only two of the detents are shown in the figure, a third detent is typically positioned symmetrically on the base 11 across from the detent 20. Detent 18 is disposed on deformable region 14 between grooves 12 on the base 11. The detents 18, 20 engage the annular flange (28 of FIG. 1) when the introducer 30 is seated in the sleeve 10. Because the grooves 12 reduce the structural integrity, in some embodiments, it may be necessary to make detent 18 larger than detents 20 to ensure engagement even if the flexibility caused by the grooves 12 results in deformable region 14 holding less tightly against the annular flange 28. Notably, even with grooves 12, sleeve 10 would be suitable for a wingless catheter provided that the detents 18, 20 provide sufficient holds so that the sleeve 10 does not easily become unintentionally disengaged.

FIG. 3 is a partial cross-section view of the catheter assembly and sleeve of the embodiment of FIG. 1. As shown in FIG. 1, detent 18 engages annular flange 28, and the wings 24 are seated in the slot 12 such that pressure on the distal end of arm 16 results in maximum translation away from the axis of the sleeve 10. Arm 16 has a thickness 40, which is greater than the distance 42 between the arm 16 and the body 13 of sleeve 10. In one embodiment, the arm 16 is approximately aligned with detent 18. By keeping the distance between the arm 16 and the body 13 of the sleeve, less than the thickness of the arm, inadvertent nesting, or interlocking of sleeves during manufacture is prevented.

Figure 4:
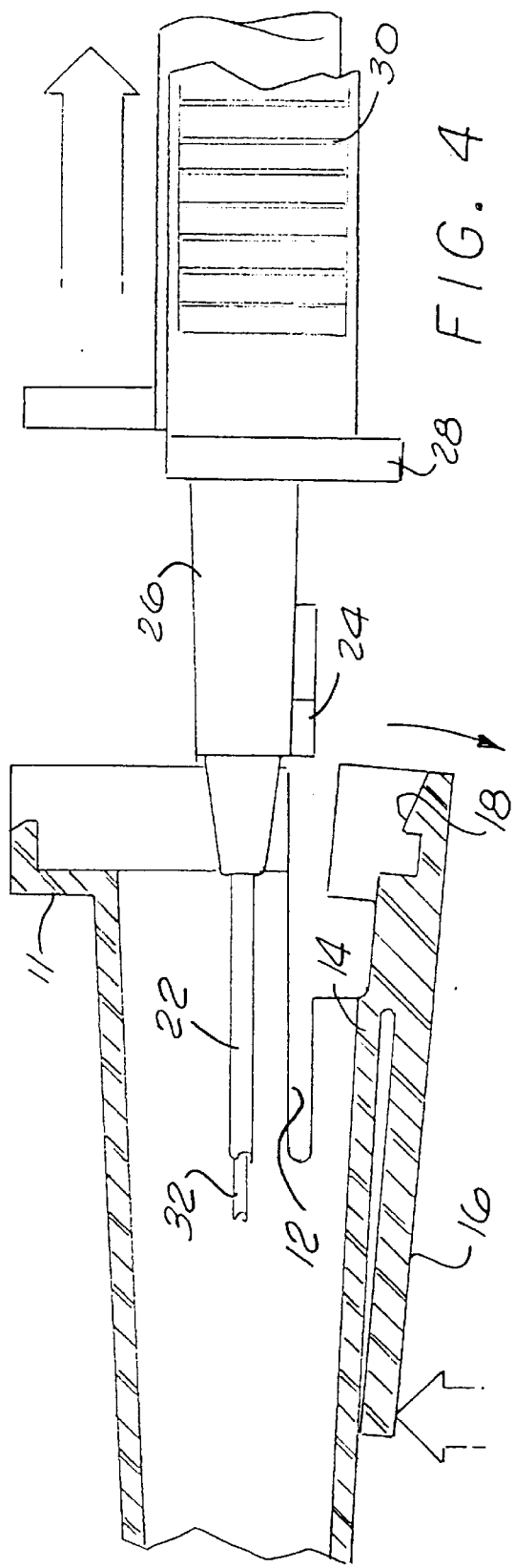
FIG. 4 is a partial sectional view of a sleeve and catheter assembly of FIG. 3 with the arm depressed, thus releasing the detent

FIG. 4 is a partial sectional view of a sleeve and catheter assembly of FIG. 3 with the arm depressed, thus releasing the detent. In this view, pressure is shown as being applied to the distal end of arm 16, thereby releasing the engagement of detent 18 from annular flange 28. Once detent 18 releases annular flange 28, the remaining detents 20 provide little or no holding force and the catheter assembly may be easily withdrawn from the sleeve without the recoil risk present in the prior art.

Figure 5:
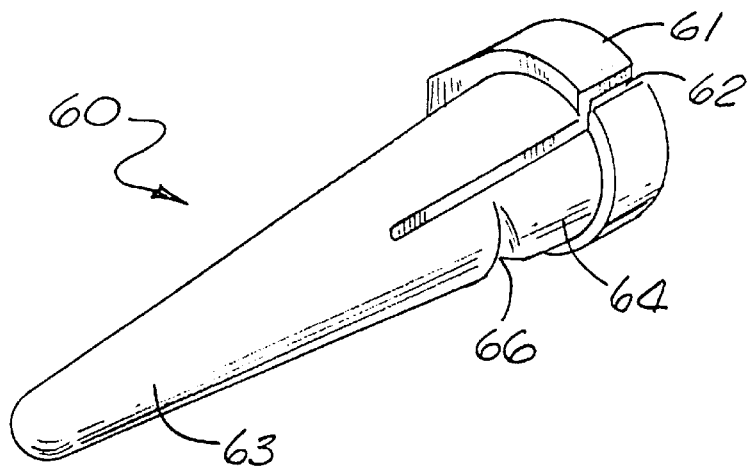
FIG. 5 is a perspective view of an alternative embodiment of the invention.

FIG. 5 is a perspective view of an alternative embodiment of the invention. Sleeve 60 has a base 61 coupled to a shaft 63, and a pair of grooves 62 define a deformable region 64 therebetween. A thin or flexible region 66 is provided partway down the deformable region 64. Flexible region 66 is flexible relative to the remainder of deformable region 64. This may be accomplished by making flexible region 66 of the same material as the rest of the deformable region 64, only thinner. Alternatively, different material having different rigidities may be used. The detents (not shown) within the base 61 are as previously described.

Figure 6:
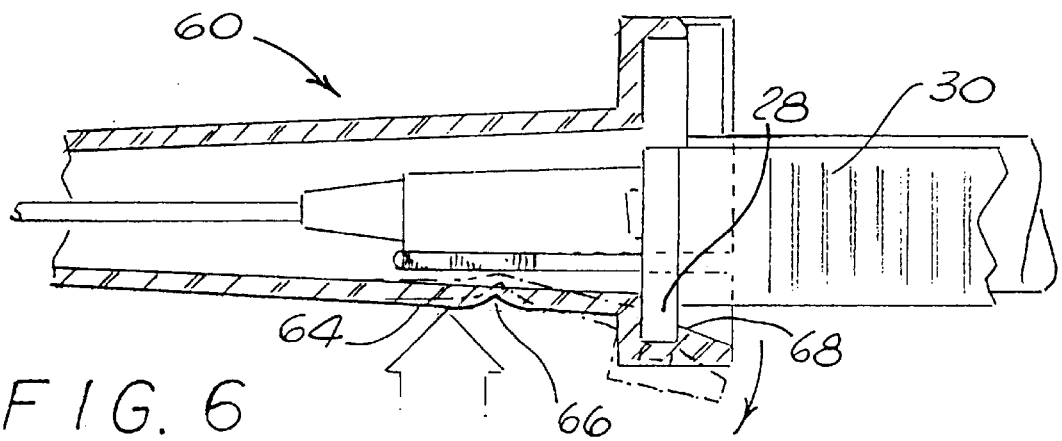
FIG. 6 is a partial cross-sectional view of the sleeve of FIG. 5 with a catheter assembly inserted therein.

FIG. 6 shows a partial cross-sectional view of the sleeve of FIG. 5 with a catheter assembly inserted therein. Pressure on the deformable region 64 distal to the thin region 66 causes detent 68 on the base within the deformable region to translate away from the axis of the sleeve and disengage from annular flange 28 of the introducer 30.

Figure 7:
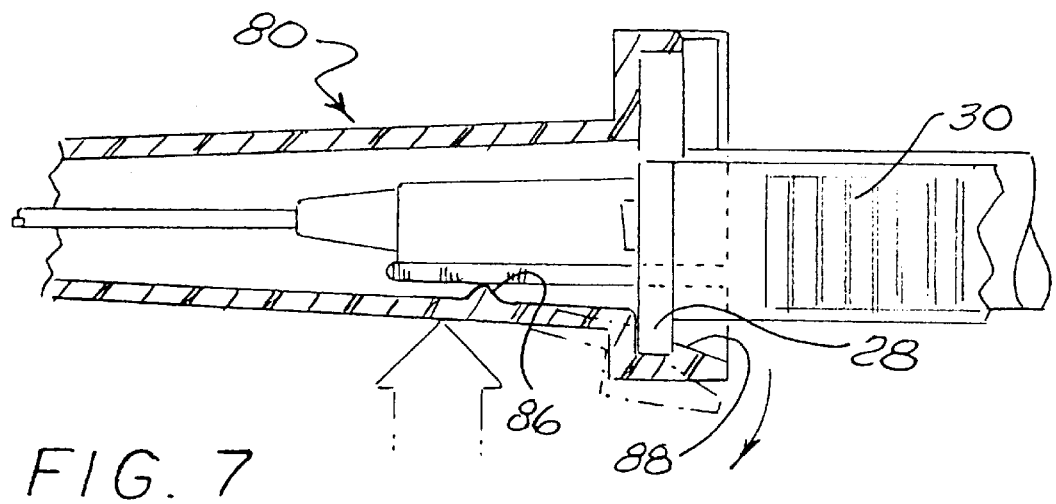
FIG. 7 is a partial sectional view of a third alternative embodiment of the sleeve installed on a catheter assembly.

FIG. 7 is a partial sectional view of a third alternative embodiment of the sleeve installed on a catheter assembly. This embodiment is similar to the embodiment of FIGS. 5 and 6, except that a pivot protrusion 86 is provided on the inner surface of the sleeve within the deformable region 84. The pivot protrusion 86 contacts the catheter hub, such that pressure on the deformable region 84 distal to the pivot protrusion 86 causes the deformable region 84 to act like a teeter-totter about the pivot protrusion, such that the detent 88 translates away from the axis of the sleeve and disengages from annular flange 28.

Each of the described embodiments permits the introducer catheter assembly to be withdrawn from the sleeve with little or no resistance. The sleeve could be injection molded or formed in any other conventional means. In one embodiment, the entry sleeve is integrally formed as one continuous unit. Notably, the sleeves described above with the grooves, are suitable for many types of catheters, including both winged and wingless catheters. Thus, a single sleeve design can be used for a wide variety of different catheters, thereby reducing the tooling and manufacturing costs which would otherwise be necessary to produce the several different sleeve types.

In the foregoing specification, the invention has been described with reference to specific embodiments thereof. It will, however, be evident that various modifications and changes can be made thereto without departing from the broader spirit and scope of the invention as set forth in the appended claims. The specification and drawings are, accordingly, to be regarded in an illustrative rather than a restrictive sense. Therefore, the scope of the invention should be limited only by the appended claims.

What is claimed is:

1. An apparatus comprising:
   a sleeve having a body portion at a distal end and a base at an insertion end, the sleeve and base defining two grooves at the insertion end, the grooves along the two sides of a deformable region of the sleeve;
   a shoulder portion disposed in said base wherein the passageway through the sleeve narrows towards the distal end at said shoulder portion;
   a plurality of detents disposed on an inside of the base, the plurality of detents to engage an annular flange of an item sleeved; and
   an arm coupled to the sleeve between the grooves and approximately aligned with one detent of the plurality of detents.

2. The apparatus of claim 1 wherein the arm is coupled to the deformable region at a first end adjacent to the base and has a free end more distant from the base along the sleeve.

3. The apparatus of claim 1 wherein the apparatus is integrally formed as a single unit.

4. The apparatus of claim 2 wherein the arm has a thickness and wherein a gap between the arm and the deformable region is less than the thickness of the arm.

5. The apparatus of claim 1 wherein the plurality of detents define vertices of a triangle, with one vertex located on the base between the grooves.

6. A catheter sleeve comprising:
   a base at one insertion end;
   a body coupled to the base and extending therefrom to a distal end, the body and the base defining a first groove and a second groove;
   a shoulder portion disposed in said base wherein the passageway in the sleeve narrows towards the distal end at said shoulder portion
   a first detent disposed on the inside of the base between the first groove and the second groove; and
   means for releasing the first detent from an engagement position.

7. The catheter sleeve of claim 6 wherein the means for releasing comprises:
   an arm adjacent to the base coupled between the grooves and extending toward the distal end of the body, a free end of the arm separated from the body by a gap.

8. The catheter sleeve of claim 7 wherein the arm has a thickness and wherein the gap is less than the thickness.

9. The catheter sleeve of claim 6 wherein the means for releasing comprises:
   a stiff region between the grooves adjacent to the base; and
   a flexible region between the grooves adjacent to the stiff region and remote from the base.

10. The catheter sleeve of claim 6 wherein the means for releasing comprises:
    a pivot protrusion disposed between the grooves within the body, the pivot protrusion to contact a hub of a catheter when a catheter is within the sleeve, such that pressure applied between the grooves and distal to the pivot protrusion causes the first detent to translate away from an annular flange of an introducer.

\* \* \* \* \*